United States Patent
Langlois et al.

(10) Patent No.: US 8,555,715 B2
(45) Date of Patent: Oct. 15, 2013

(54) GROUND CONTACT SENSING SYSTEMS AND METHODS FOR LOWER-LIMB ORTHOTIC AND PROSTHETIC DEVICES

(75) Inventors: David Langlois, St-Jacques-de-Leeds (CA); David Landry, St-Jean-Chrysostome (CA); Benoit Gilbert, Lac-Beauport (CA)

(73) Assignee: Össur hf., Reykjavík (IS)

( * ) Notice: Subject to any disclaimer, the term of this patent is extended or adjusted under 35 U.S.C. 154(b) by 95 days.

(21) Appl. No.: 13/178,046

(22) Filed: Jul. 7, 2011

(65) Prior Publication Data

US 2012/0010729 A1    Jan. 12, 2012

Related U.S. Application Data (60) Provisional application No. 61/362,024, filed on Jul. 7, 2010.

(51) Int. Cl.
*A61B 5/00*    (2006.01)

(52) U.S. Cl.
USPC ................................. 73/172; 623/50; 73/760

(58) Field of Classification Search
USPC ...................................... 73/172, 760; 623/50
See application file for complete search history.

(56) References Cited

U.S. PATENT DOCUMENTS

| | | | |
|---|---|---|---|
| 5,383,939 A | 1/1995 | James | |
| 5,406,845 A * | 4/1995 | Berger et al. | 73/379.09 |
| 6,443,993 B1 * | 9/2002 | Koniuk | 623/24 |
| 6,500,210 B1 | 12/2002 | Sabolich et al. | |
| 6,610,101 B2 | 8/2003 | Herr et al. | |
| 6,918,308 B2 | 7/2005 | Biedermann et al. | |
| 7,137,998 B2 | 11/2006 | Bedard | |
| 7,147,667 B2 | 12/2006 | Bedard | |
| 7,198,071 B2 * | 4/2007 | Bisbee et al. | 141/8 |
| 7,410,471 B1 | 8/2008 | Campbell et al. | |
| 7,475,606 B2 | 1/2009 | Selig et al. | |
| 7,500,407 B2 | 3/2009 | Boiten | |
| 7,597,017 B2 * | 10/2009 | Bedard et al. | 73/866.4 |
| 7,655,050 B2 | 2/2010 | Palmer | |
| 7,736,394 B2 | 6/2010 | Bédard et al. | |
| RE42,903 E | 11/2011 | Deffenbaugh et al. | |
| 2002/0094919 A1 * | 7/2002 | Rennex et al. | 482/124 |
| 2004/0086240 A1 * | 5/2004 | Togami et al. | 385/92 |
| 2005/0107889 A1 | 5/2005 | Bedard et al. | |
| 2006/0136072 A1 | 6/2006 | Bisbee et al. | |
| 2006/0206215 A1 | 9/2006 | Clausen et al. | |
| 2008/0046096 A1 | 2/2008 | Bedard et al. | |
| 2008/0276725 A1 | 11/2008 | Pusch | |
| 2009/0299480 A1 | 12/2009 | Gilbert et al. | |
| 2010/0185124 A1 | 7/2010 | Bisbee, III et al. | |
| 2011/0125290 A1 | 5/2011 | Langlois | |

OTHER PUBLICATIONS

PCT/US 11/43246 International Search Report and the Written Opinion of the International Searching Authority, or the Declaration, dated Nov. 21, 2011.

* cited by examiner

*Primary Examiner* — Max Noori
(74) *Attorney, Agent, or Firm* — Knobbe, Martens, Olson & Bear LLP (57) ABSTRACT

A method of sensing ground contact with a lower limb prosthetic or orthotic device is provided. A first translational displacement between a frame and a connector can be sensed and then processed to identify an axial load caused by heel-ground contact. Additionally, a second translational displacement between the frame and the connector can be sensed and then processed to identify a torsional load caused by toe-ground contact.

20 Claims, 10 Drawing Sheets

GROUND CONTACT SENSING SYSTEMS AND METHODS FOR LOWER-LIMB ORTHOTIC AND PROSTHETIC DEVICES

CROSS-REFERENCE TO RELATED APPLICATIONS

This application claims the priority benefit under 35 U.S.C. §119(e) to U.S. Provisional Patent Application Ser. No. 61/362,024 (filed 7 Jul. 2010), the entirety of which is hereby expressly incorporated by reference herein.

BACKGROUND

1. Field

This application generally relates to systems and methods for sensing ground contact by prosthetic and/or orthotic devices.

2. Description of the Related Art

Advent of computer-controlled lower-limb prosthetic devices has made available to the lower-limb amputee an unprecedented realm of performance. The extent of the lower-limb locomotion tasks associated with daily living activities often cannot be addressed with a single lower-limb prosthetic device behavior. While non-computer controlled devices are relying on mechanical linkages, or mechanisms, which properties can hardly be modified to change their behavior, computer-controlled devices are quite more flexible, and assuming sufficient control of their actuation mechanism, can sustain a very large realm of lower-limb joint behaviors. For computer controlled lower-limb prosthetic devices to be able to vary their behavior in an appropriate and efficient manner, devices can be equipped with a sensor set allowing the embedded processor and control scheme to extract relevant information from the environment in which they are evolving and apply the behavior changes accordingly.

One area where computer-controlled lower-limb prosthetics are showing improved performance over passive or non-computer controlled devices is in the management of the dual mechanical configuration of the lower-limb joints during gait related activities. As the lower-limb transitions from the aerial phase to the ground contacting phase, lower-limb joints are observed to drastically change their behavior, going from a low mechanical impedance state during the aerial phase to a high impedance state during the contacting phase. Proper management of this joint behavior modification significantly improves lower-limb prosthetic devices usability and performance from a user standpoint. Moreover, management of such a transition is based on the system's capacity to know with accuracy and reliability whether or not the prosthetic foot is in contact with the ground.

Development of sensors allowing for ground contact detection in a robust and reliable manner represents a significant aspect of computer-controlled lower-limb prosthetic devices. In fact, many technologies are available to perform such detection, but all present limitations. Load cells are commonly used to perform this task, but are bulky, heavy and need periodical calibration to ensure that their no-load reading remains constant. Accelerometers are compact and allow for monitoring foot strike shocks, but only provide a contextual measure in the sense that if a specific event is missed, you have to wait to the next one to know for sure in which configuration the prosthetic limb is. Piezoelectric sensors are also compact, but present limited performance as far as DC measurement capacity is concerned. Resistive ink sensors can also be used to measure occurrence of foot strike in prosthetic system, but these are known to be fragile and present only a limited life duration in typical field operating conditions.

Moreover, development of a robust sensor system for ground contact detection requires a system simple enough where a priori information and assumptions are required to draw a conclusion on the actual lower-limb mechanical configuration. Hence, benefits arise at a system level if the ground contact sensor design itself is able to reject external perturbation and provides a measure showing high correlation with foot strike and only limited correlation with other loads affecting the system during typical operation. More specifically, computer-controlled devices with active actuation are subject to perturbation created by the foot inertia, as the system attempts to control the hip, knee or ankle behavior.

SUMMARY

Certain embodiments disclosed herein include a ground contact sensor for prosthetic devices where sensitivity to inertial (i.e., torque) loading is reduced through use of a selectively compliant mechanical structure, allowing at the same time sufficient compliance in the axial direction to properly measure occurrence of the foot strike event using a low-cost sensor.

Additional embodiments disclosed herein are related to ground contact sensing for lower-limb prosthetic or orthotic devices. Ground contact sensing can be an important source of information to perform robust and high performance control of lower-limb prosthetic or orthotic devices. Fundamentally, devices that implement stance phase control often require some sort of ground contact sensing, while swing phase control devices can often do without ground contact sensing, but are also shown to be more robust when equipped with such type of sensing. Embodiments herein described present a ground contact sensor wherein a selectively compliant mechanical structure is used to minimize the impacts of swing phase inertial perturbation on the sensor output, such that swing and stance phases are properly detected in a robust and timely manner.

In certain embodiments, a ground contact sensor is disclosed for prosthetic or orthotic devices wherein selective sensitivity is achieved through the use of a selectively compliant mechanical structure, which provides high stiffness to sagittal plane torque loading (e.g., foot generated inertial effects) while being highly compliant under axial loading. In certain embodiments, the selectively compliant mechanical structure comprises one or more of the following features:

Two blade sets, each blade set being composed of two group of blades vertically separated by a predetermined distance and aligned in an anterior-posterior fashion in the device assembly, the two blade sets being positioned on the medial and lateral sides of the assembly vertical centerline;

A single plate set composed of two groups of plates vertically separated by a predetermined distance and positioned so as to be centered on the device long axis in the anterior-posterior and medial-lateral directions;

Two serially connected four-bars linkages connected to the frame through their free ends;

Blade sets or plates made of multiple diamond coated thin steel parts;

Blade sets or plates made of multiple thin steel parts;

The selectively compliant mechanical structure connecting a sensor moving part to a fixed part through a friction joint;

The selectively compliant mechanical structure connecting the sensor moving part to the fixed part through a pinned joint showing no play; and The fixed part and the moving parts being machined in a single block.

In certain further embodiments, a ground contact sensor for prosthetic or orthotic devices is disclosed wherein axial displacement of the sensor moving part is representative of the ground contact occurrence. In certain embodiments, the sensor moving part axial displacement is detected and/or measured with one or more of the following: load cell, non-contact magnetic sensor, optical encoder, mechanical switch, magnetic switch; inductive sensor, capacitive sensor, magnetic encoder, reflective infrared sensor, piezoelectric sensor and conductive rubber. In certain further embodiments, a motion-controlled prosthetic or orthotic system is disclosed comprising at least one ground contact sensor as disclosed herein, wherein the ground contact sensor is integrated with and/or couple to a prosthetic or orthotic device (e.g., a knee device).

In certain embodiments, a method is disclosed for detecting or analyzing a user's gait utilizing at least an embodiment of a ground contact sensor as disclosed herein. In yet further embodiments, a method is disclosed for adjusting a motion-controlled prosthetic or orthotic device based on information received from at least an embodiment of a ground contact sensor as disclosed herein.

In further embodiments, a prosthetic knee device can include a tibial shank, a distal connector, and a load sensor. The tibial shank can extend along a longitudinal axis from a proximal end to a distal end, with a proximal connector attached to the proximal end of the tibial shank. The proximal connector can be configured to operatively couple the tibial shank to a socket of an amputee. The distal end of the tibial shank can define a recessed portion. The distal connector can be movably attached to the distal end of the tibial shank. At least a portion of the distal connector can be disposed within the recessed portion of the tibial shank, and be axially and pivotally movable relative to the distal end of the tibial shank. Further, the distal connector can be configured to operably couple the tibial shank to a prosthetic foot. The distal connector can include two pairs of blades. The first pair of planar blades can be disposed on a medial side of the distal connector and extend in an anterior-posterior direction. Further, the first pair of planar blades can be axially spaced apart from each other. The second pair of planar blades can be disposed on a lateral side of the distal connector and extending in the anterior-posterior direction. Further, the second pair of planar blades can be similarly axially spaced apart from each other. The first and second pair of blades can be disposed in the recessed portion of the tibial shank when the distal connector is attached to the tibial shank and be configured to resiliently flex when the prosthetic knee is subjected to a load. The load sensor can be disposed in the recessed portion and be in operative contact with the tibial shank and the distal connector. Thus, the load sensor can be configured to sense relative movement between the distal connector and the tibial shank during operation of the prosthetic knee. Thus, the distal connector can axially displace relative to the tibial shank when the prosthetic knee is subjected to an axial load along the longitudinal axis such that at least a portion of the first and second pair of blades flex. The load sensor can then sense said axial displacement between the distal connector and the tibial shank. Further, the distal connector can rotate about a second axis, perpendicular to the longitudinal, axis relative to the tibial shank when the prosthetic knee is subjected to a torsional load such that at least a portion of the first and second pair of blades flex. The load sensor can then sense said torsional displacement.

In a further embodiment, a lower limb prosthetic or orthotic device can define a longitudinal axis and include a sensor mounted within said lower limb prosthetic device. The sensor can include a frame portion and a connector. The frame portion can include two or more non-moving abutment surfaces disposed on an anterior side and a posterior side of the frame portion, and a load cell at least partially disposed in the frame portion and having a first end mounted to the frame portion and a second end. The connector can be movably attached to the frame portion and include a connector main body and a load cell receiving portion. The connector main body can be configured to receive a load and include two or more moveable abutment surfaces generally adjacent to the non-moving abutment surfaces to allow a limited displacement between the abutment surfaces. The connector can then move relative to the frame portion by the same limited displacement. The load cell receiving portion can be configured to mount to the second end of the load cell such that the load cell can sense relative movement between the connector and frame portion. With these features, an axial load applied to the lower limb device can cause the connector to move relative to the frame portion and the moving abutment surfaces to move relative to the non-moving abutment surfaces said limited displacement, which can cause a first displacement sensed by the load cell. Further, a torsional load applied to the lower limb device can cause the connector to rotate relative to the frame portion and at least one moving abutment surface to move relative to the corresponding non-moving abutment surface said limited displacement, which can cause a second displacement sensed by the load cell different from the first displacement.

In a further embodiment, a method of sensing ground contact with a lower limb prosthetic or orthotic device is provided. A first translational displacement between a frame and a connector can be sensed and then processed to identify an axial load caused by heel-ground contact. Additionally, a second translational displacement between the frame and the connector can be sensed and then processed to identify a torsional load caused by toe-ground contact.

In a further embodiment, a ground-contact sensor can include a non-moving body and a moving body. The non-moving body can include two or more non-moving abutment surfaces disposed on separate sides of the non-moving body and a load cell mounted to the non-moving body at a first end and include a second end. The moving body can be configured to receive a load and include two or more abutment surfaces and a load cell receiving portion. The two or more moving abutment surfaces can be disposed generally adjacent to the non-moving abutment surfaces to allow a limited displacement between the abutment surfaces, at the abutment surfaces. The load cell receiving portion can be disposed generally between the abutment surfaces and operatively mount to the second end of the load cell such that the load cell can sense a relative displacement between the non-moving and moving bodies. With these features, an axial load applied to the moving body can cause the moving body to move relative to the non-moving body and the moving abutment surfaces to move relative to the non-moving abutment surfaces said limited displacement, which can cause a first displacement sensed by the load cell. Further, a torsional load applied to the lower limb device can cause the moving body to rotate relative to the non-moving body and the at least one moving abutment surface to move relative to the corresponding non-moving abutment surface said limited displacement, which can cause a second displacement sensed by the load cell different from the first displacement.

In a further embodiment, a ground contact sensor for a prosthetic or orthotic device can include a connector and a load sensor. The connector can include two pairs of planar blades. Further, the connector can be movably attachable to a frame portion of the prosthetic or orthotic device and be axially and pivotally movable relative to the frame portion. The first pair of planar blades can be disposed on a medial side of the distal connector and extend in an anterior-posterior direction. The first pair of planar blades can further be axially spaced apart from each other. The second pair of planar blades can be disposed on a lateral side of the distal connector and extend in the anterior-posterior direction. The second pair of planar blades can further be axially spaced apart from each other. The first and second pair of blades configured to resiliently flex when the prosthetic or orthotic device is subjected to a load. The load sensor receiving portion can be configured to couple to a load sensor on the prosthetic or orthotic device. Further, the load sensor can be configured to sense relative movement between the connector and the frame portion during operation of the prosthetic or orthotic device. The connector can be configured to axially displace relative to the frame portion when the frame portion is subjected to an axial load such that at least a portion of the first and second pair of blades flex. The load sensor can sense this axial displacement between the connector and the frame portion. The connector can also be configured to rotate about a second axis, perpendicular to the longitudinal axis, relative to the frame portion when the frame portion is subjected to a torsional load such that at least a portion of the first and second pair of blades flex. The load sensor can sense this rotation.

In a further embodiment, a ground contact sensor includes a non-moving portion, a moving portion, and a load sensor between said portions. The moving portion can be configured to axially displace relative to the non-moving portion when the sensor is subjected to an axial load. The load sensor can sense said axial displacement between the moving portion and the non-moving portion. The moving portion can also rotate about a second axis, perpendicular to the longitudinal axis, relative to the non-moving portion when the non-moving portion is subjected to a torsional load such that at least a portion of the first and second pair of blades flex. The load sensor can also sense said rotation.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

DETAILED DESCRIPTION OF CERTAIN PREFERRED EMBODIMENTS

Certain embodiments described herein relate to a computer controlled lower-limb prosthesis, whether or not it is actuated, motorized, or fully passive. Further embodiments can also be used in other contexts, such as for certain types of lower-limb orthotic devices.

Figure 1:
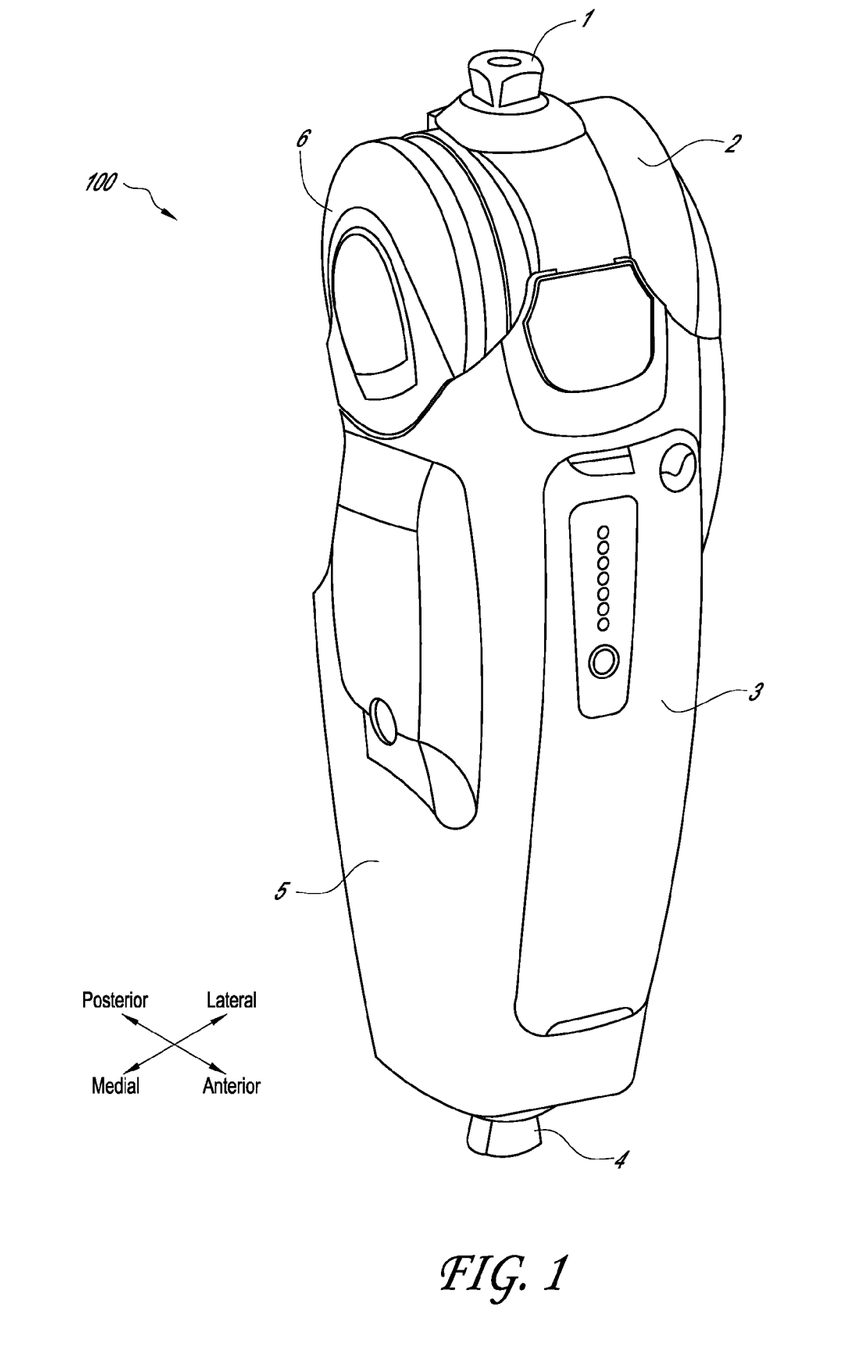
FIG. 1 is a perspective view of a prosthetic knee device.

FIG. 1 illustrates one embodiment of a motorized lower-limb prosthesis 100 that can be integrated with the ground contact sensing systems described herein. It is to be noted that this specific embodiment is provided as an example and the scope of the inventions herein described apply to other embodiments, such as prosthetic feet, lower limb orthotics, sensors for non-prosthetic or orthotic use, and other devices.

The motorized lower-limb prosthesis 100 of depicted in FIG. 1 implements a knee joint and is typically connected to the user's residual limb through a socket (not shown) via the proximal end male pyramid connector 1 present on its proximal extremity. The proximal male pyramid connector 1 is secured to a knee actuator housing 2, which can rotate with respect to a prosthetic device shank section 5. Rotation of an actuator output lever 6 causes rotation of the knee actuator housing 2 and, consequently, the male pyramid connector 1. Shank section 5 contains electronic components (not shown) required for the system to operate, although in other embodiments these components can be located elsewhere, such as on a peripheral device or within the components further described below. The battery unit 3 can provide power to the aforementioned electronic components. The shank section 5 of the prosthetic knee can then connect to ankle or foot components (not shown) through the distal end male pyramid connector 4.

Thus, the motorized lower-limb prosthesis can connect to a user (e.g., via the socket) on a proximal end of the prosthesis and connect to the ankle/foot on the distal end of the prosthesis. In some embodiments, the sensors described herein can be used to control a device such as a prosthetic or orthotic device. Additional details regarding embodiments of a motorized knee prosthesis usable with systems and apparatus described herein are disclosed in U.S. Patent Application Publication No. 2009-0299480 A1, entitled "Joint Actuation Mechanism for a Prosthetic and/or Orthotic Device Having a Compliant Transmission," which is hereby incorporated herein by reference in its entirety and should be considered part of this specification.

Figure 2:
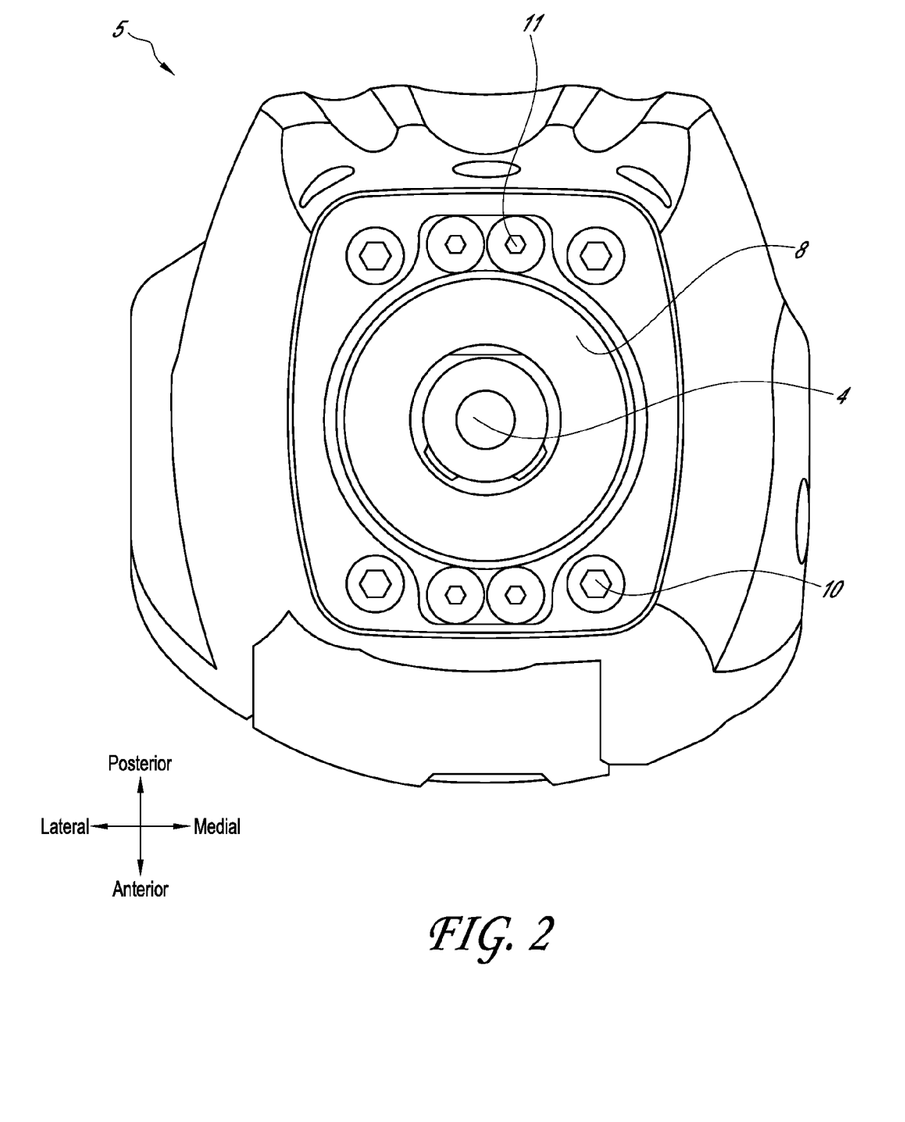
FIG. 2 is a bottom view of the prosthetic knee device of FIG. 1.

FIG. 2 presents a detailed view of the distal end of the motorized knee prosthesis of FIG. 1, where certain external components of a ground contact sensor are identified. The embodiment disclosed in FIG. 2 is located in the distal part of the tibial shank section 5 of the lower-limb prosthetic device, although in other embodiments it could be disposed in other sections, such as at a proximal part of the tibial shank section 5, at a proximal portion of the knee prosthesis 100 (e.g., at the proximal connector 1, or on another device (as discussed above).

The shank section 5 of the knee prosthesis depicted in FIGS. 1 and 2 operatively connects to a distal connector dome 8 by way of the ground contact sensor described herein. The distal dome connector 8 can form a portion of a moving portion 102 of a ground contact sensor, moving with respect to the shank section 5 (which can be considered a non-moving portion), as further described below. The distal pyramid connector 4 can be fixed to the distal connector dome 8 and be used to rigidly connect various ankle and/or foot components to the knee prosthesis 100, more particularly to the moving portion 102 of the ground contact sensor of the knee prosthesis 100. The distal dome connector 8 is fastened to backing plates 32, 36 (depicted in FIGS. 7 and 8) through flat head cap screws 11 that prevent the connector from being pulled out of the shank section 5 when torque or tension forces are applied on a prosthetic foot used with the device. Screws such as socket head cap screws 10 are used to rigidly fasten the ground contact sensor internal components to the prosthetic device shank 5 (e.g., to a frame of the shank).

Figure 3:
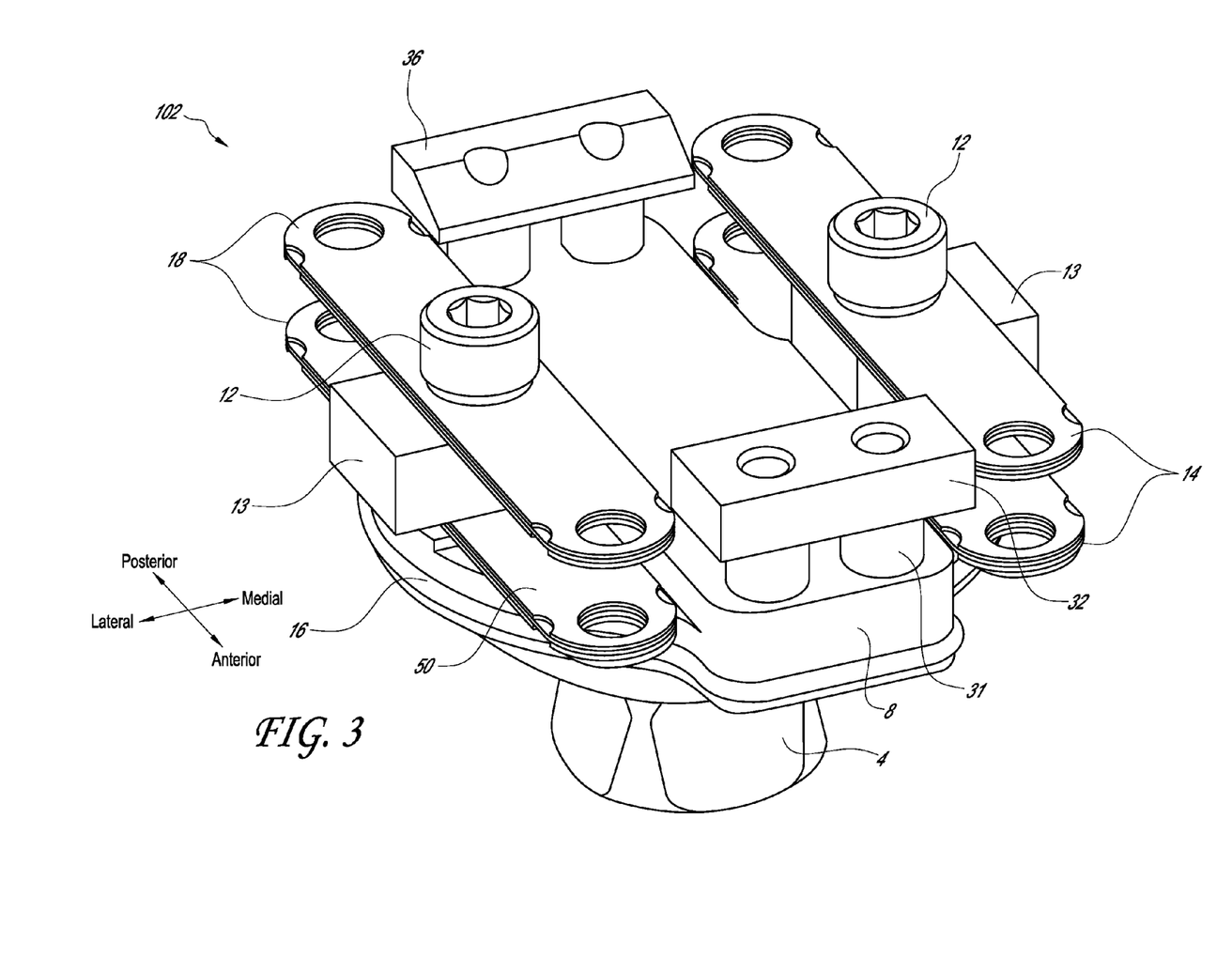
FIG. 3 is a perspective view of a moving portion of a ground contact sensor of the prosthetic knee device of FIG. 1.
Figure 4:
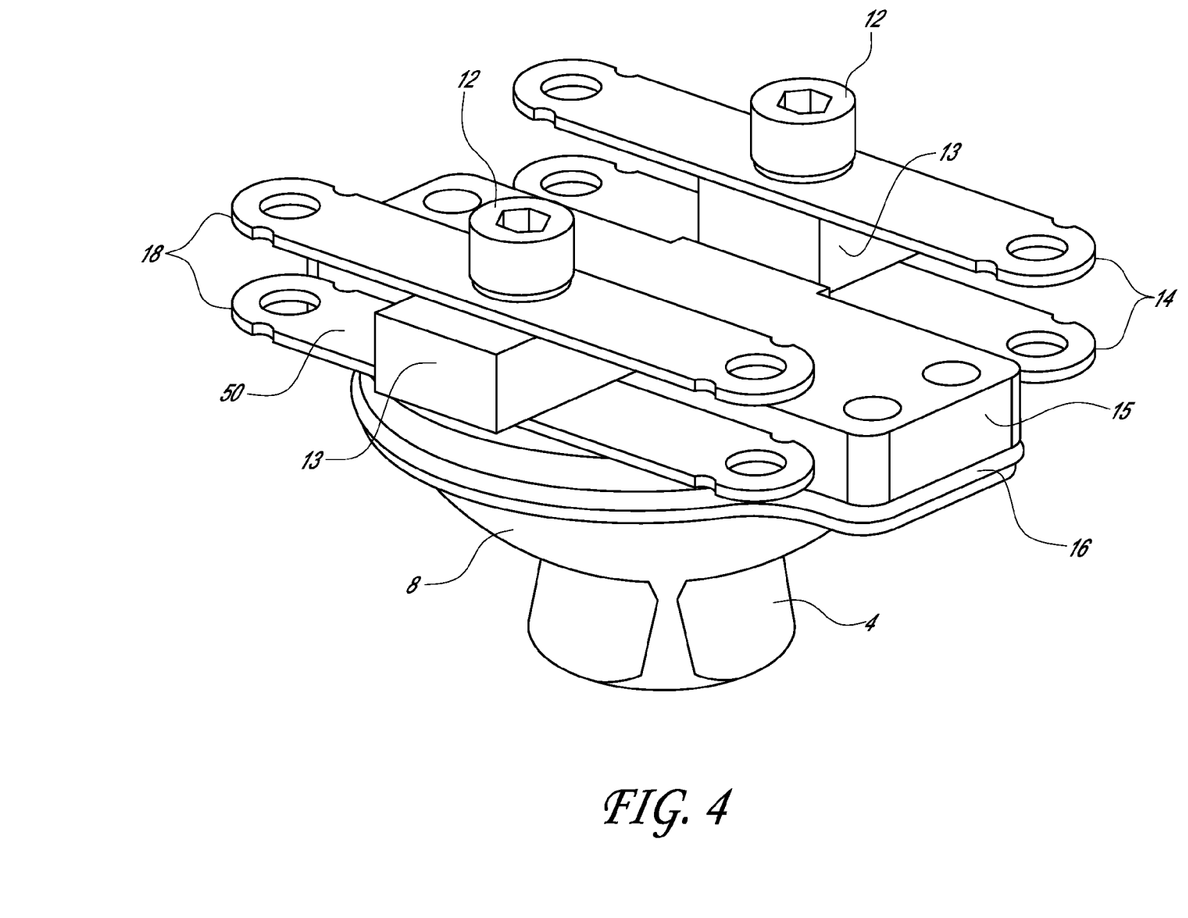
FIG. 4 is a perspective view of a sub-portion of the moving portion of FIG. 3.

FIG. 3 illustrates the moving portion 102 of the sensor, and FIG. 4 illustrates certain sub-components thereof. The moving portion 102 can include a main body such as the distal dome connector 8, which can include or be connected to a male pyramid connector 9. As illustrated, attached to the distal dome connector 8 and the male pyramid connector 4 are blade sets 14 and 18, which can form generally elongated bodies. The blade sets 14, 18 are illustrated to include two blades each, which are vertically offset by a predetermined distance, which in this specific example is set to the thickness of two side blocks 13. A vertical offset between the blade groups 14, 18 can increase the assembly stiffness when a torque load is applied to the male pyramid connector 4, while allowing the assembly to be very compliant to axial loads. The mechanical structure created by the assembly of the blade groups on top and bottom of the side blocks 13 can then create a selectively compliant mechanical structure. The side blocks 13 can also be designed to exceed (e.g., protrude from) the distal dome connector's 8 width in the medial-lateral direction.

Figure 6:
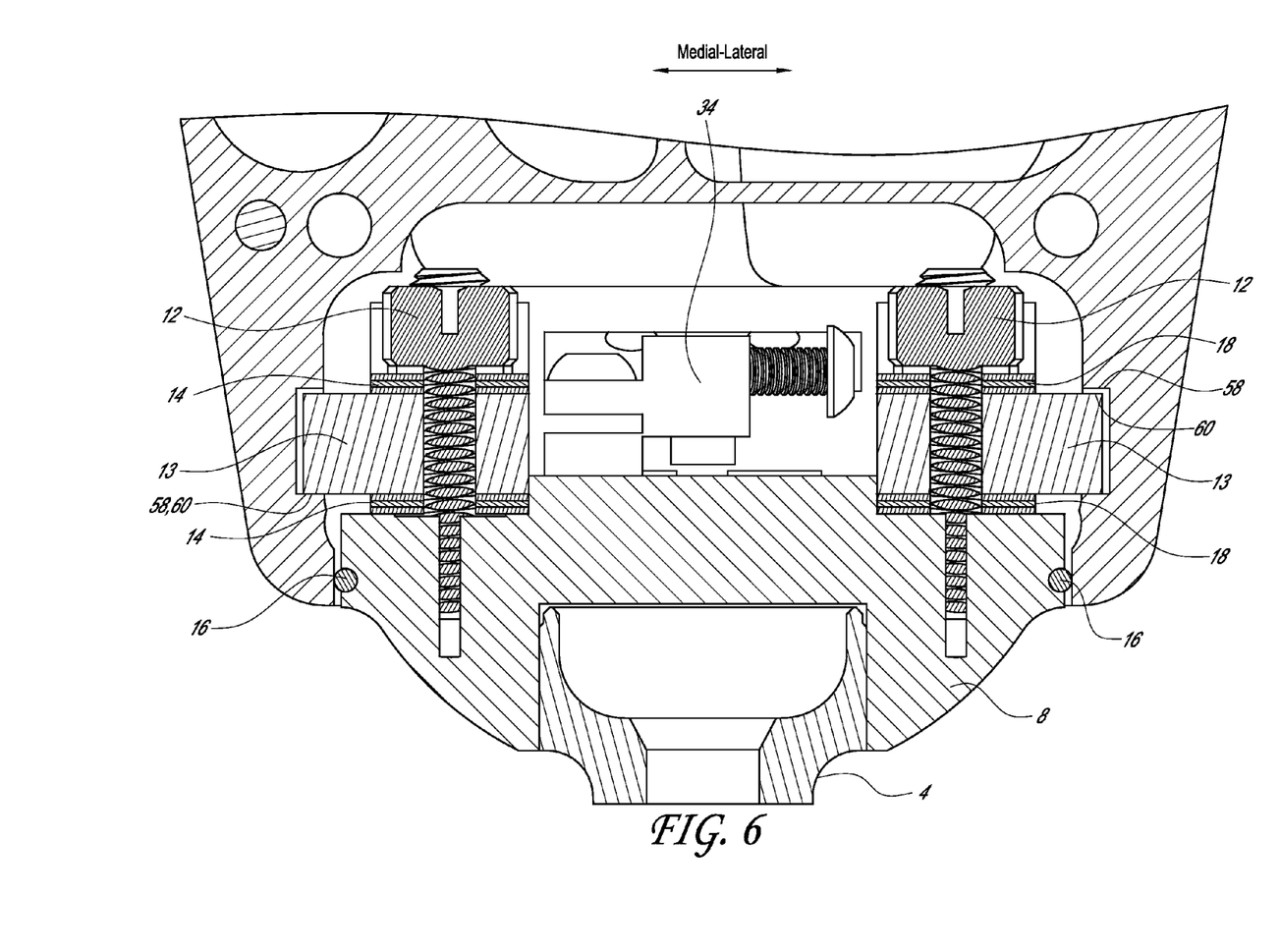
FIG. 6 is a coronal cross-section of the ground contact sensor of the prosthetic knee device of FIG. 1.

Once assembled in the shank section's 5 frame, the exceeding parts of the side blocks 13 can reside in slots machined in the frame. This positioning of the side blocks 13 can limit the maximum displacement of the distal dome connector 8 when the moving portion 102 of the assembly is submitted to an offset medial-lateral load or a frontal plane torque. For example, the side blocks 13 can have a thickness slightly less than the width of the slots machined in the frame, as best shown in FIG. 6. This difference in thickness/width can provide for a limited displacement between the side blocks 13 and the slots in the frame of the prosthesis 100. Thus, e.g., under an offset medial-lateral load, the side blocks 13 can move the limited displacement, and then be stopped by an interaction between abutment surfaces 58 on the side blocks 13 and, e.g., abutment surfaces 60 on the frame of the prosthesis 100. More generally, the side blocks 13 can form a portion of the moving portion 102, such that the moving portion 102 can move a limited displacement relative to a non-moving part (such as the prosthesis 100), until contact occurs between respective abutment surfaces.

In other embodiments the blade groups 14, 18 can include three blades, or some other number of blades. The number of blades in each group, as well as their thicknesses and material types can be selected based on the desired properties for the complete assembly, e.g., for axial stiffness, sagittal plane torque rejection capability, and other features. The blades sets 14 and 18, as well as the side blocks 13 are rigidly fixed to the distal dome connector 8 through screws such as socket head cap screws 12, thus forming portions of a substantially rigidly connected moving portion 102. An o-ring 16 is located on the periphery of the distal dome connector 8 in order to fill the gap between this last part and the frame parts and keep particles from entering in the knee prosthetic 100.

Figure 5:
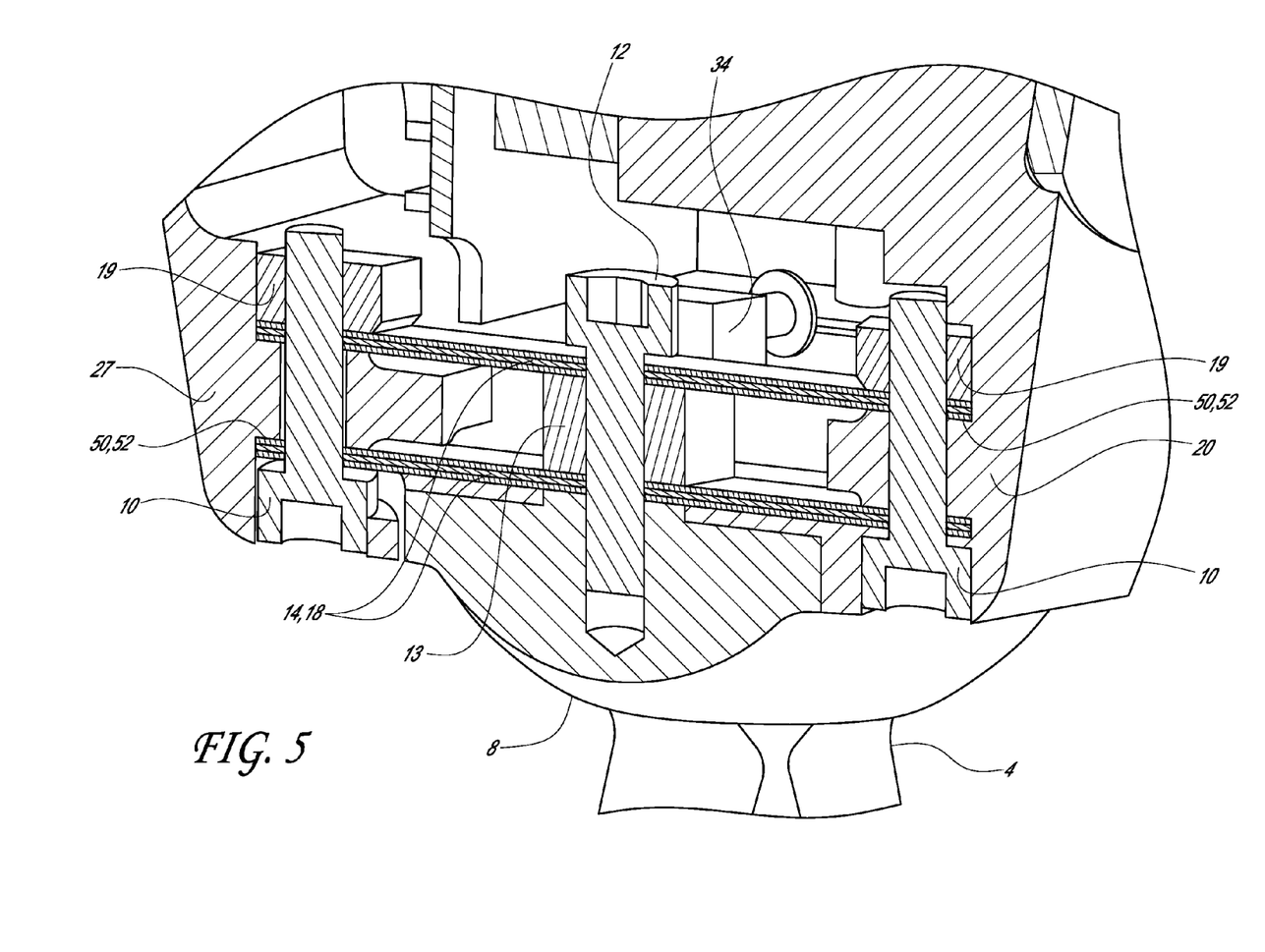
FIG. 5 is a perspective view of a sagittal off-center cross-section of the ground contact sensor of the prosthetic knee device of FIG. 1.

FIG. 5 presents an off-center cross-section of the knee prosthesis distal end, which illustrates certain moving and non-moving portions of the ground contact sensor. FIG. 6 presents a centered cross-section of the same. As shown, the blade groups 14, 18 assembled with the side blocks 13 to the distal dome connector 8 through the use of the socket head cap screws 10 are inserted in the front frame 20 and rear frame 27 of the lower limb prosthesis 100. The blade groups 14, 18 are inserted such that their abutment surfaces 50 can rest against top and bottom abutment surfaces 52 on the frame sections 20, 27, the abutment surfaces defining a thickness between them substantially similar to a thickness of the side blocks 13. The socket head cap screws 11 can then fasten to presser blocks 19 in order to press the blade groups against the frame and create a rigid friction joint between both parts. For example, in some embodiments the presser blocks 19 can be formed of a resilient material that helps to create a tight fit with the frame sections 20, 27.

To promote proper sagittal plane torque rejection and stability of the position of the moving portions in the no-load position, the blade groups 14, 18 can remain in a fixed position with respect to the non-moving portion, including the front and rear frame portions 20, 27. To promote this fixed position, diamond coated blades can be used on the top and bottom of each blade group 14, 18, increasing the strength and rigidity of the friction joint between the blades and the frame parts. Additionally or alternatively the blade groups 14, 18 can include an interference joint, reducing the requirement for the use of the friction enhancing diamond coating. An interference joint can be created to hold the blade groups 14, 18 in place through the use of press-fitted pins (not shown) instead of the socket head cap screws 10. Subsequent flexing of the blade groups 14, 18 can then be associated with movement between the moving on non-moving portions, and resistance to said flexing can similarly resist said movement.

As previously introduced, an o-ring 16 can be used to fill the gap between the distal dome connector 8 and the bore managed in the front 20 and rear 27 frames.

Figure 7:
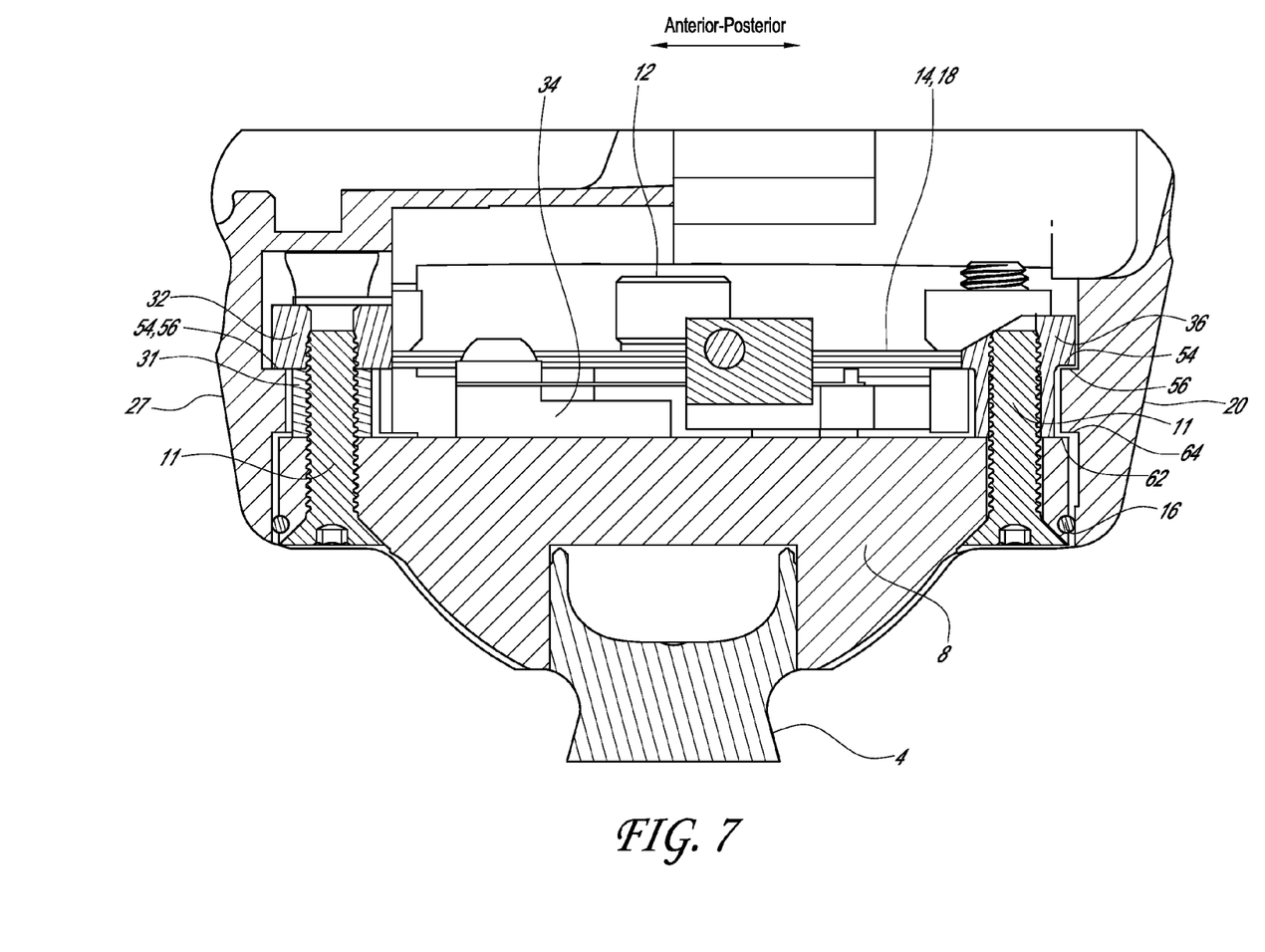
FIG. 7 is a sagittal cross-section of the ground contact sensor of the prosthetic knee device of FIG. 1.
Figure 8:
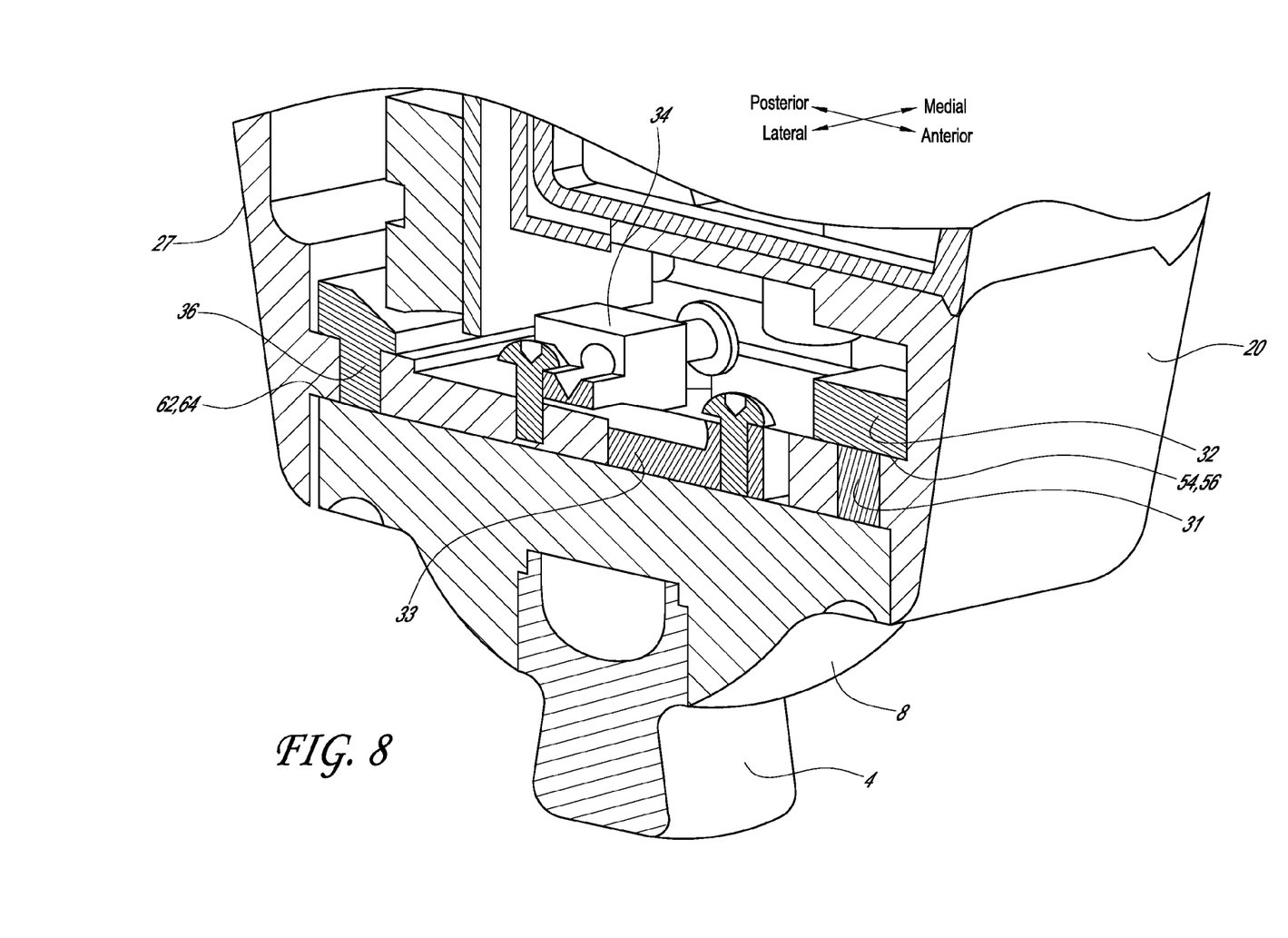
FIG. 8 is a perspective view of a coronal off-center cross-section of the ground contact sensor of the prosthetic knee device of FIG. 1.

FIGS. 7 and 8 present views of backing plates 32, 36 along with other elements of the ground contact sensor. More particularly, these views display components associated with the measurement of the axial displacement of the moving portion 102 of the ground contact sensor and the backing plates 32, 36 previously introduced. The distal dome connector 8 and the male pyramid connector 4 are mounted in the frame front 20 and rear 27 parts. Additionally, the assembly can include a rear backing plate 36, a front backing plate 32, and ground contact sensor standoffs 31 rigidly connected to the distal dome connector 8 by way of the screws 11 depicted in FIGS. 2, 7. Further, as shown, the backing plates 32, 36 can include abutment surfaces 54 that can be positioned generally adjacent abutment surfaces 56 on the front and rear frames 20, 27. However, as best shown in FIG. 7, there can be a limited amount of space between abutment surfaces on the plates 32, 36 and the frames 20, 27, providing for a limited displacement between these elements. Thus, the backing plates 32, 36 can be positioned to limit the movement of the moving portions of the ground contact sensor away from the non-moving portion, such as the frame sections 20, 27. The backing plates 32, 36 can rest on the frame parts 20, 27 to define a most external position for the moving portion of the ground contact sensor. This most external position can be achieved in the illustrated example when no load is applied on the prosthetic device 100. Movement of the moving part can then be adjusted by adjusting the length of the rear backing plate's 36 chimneys 36A and the ground contact sensor standoffs 31. For example, if these elements are made slightly longer than a corresponding frame section thickness, the moving part can provide for said motion. The movement of the moving part inside the prosthetic device 100 can also be limited by interference between the distal dome connector 8 and the frame 20, 27, e.g. by corresponding abutment surfaces on said pieces, as best shown in FIG. 7.

With this configuration, while the prosthetic device 100 is under no load, the moving portion 102 of the ground contact sensor can be extended out of the prosthetic device's frame. When a load is applied to the prosthetic device 100, the moving portion 102 can move inward or outward relative to the non-moving portions of the prosthetic device 100 such as the tibial shank 5. For example, forces can be generated by inertial loading during lower-limb acceleration and deceleration found during swing phases. As another example, such forces can be generated by sagittal plane torque, which can cause a moving force direction during stance phase that can potentially cause a portion of the moving portion 102 to move out of the non-moving portion (e.g., as shown in FIG. 6 and noted as a toe-load). Similarly, loads such as axial loads caused by ground contact can create an inward force on the moving portion 102. In certain embodiments, this motion or limited displacement of the moving part of the ground contact sensor can be less than a millimeter. Use of sub-millimeter travel distance can be advantageous as it is not perceptible by the user when operating the device and it can reduce overstressing on the blades or the friction joint, which may be higher under larger travel ranges. The distance between the distal dome connector and the frame are most visible in FIG. 5 and can be selected to be quite small (e.g., approximately 0.2 mm).

Figure 9:
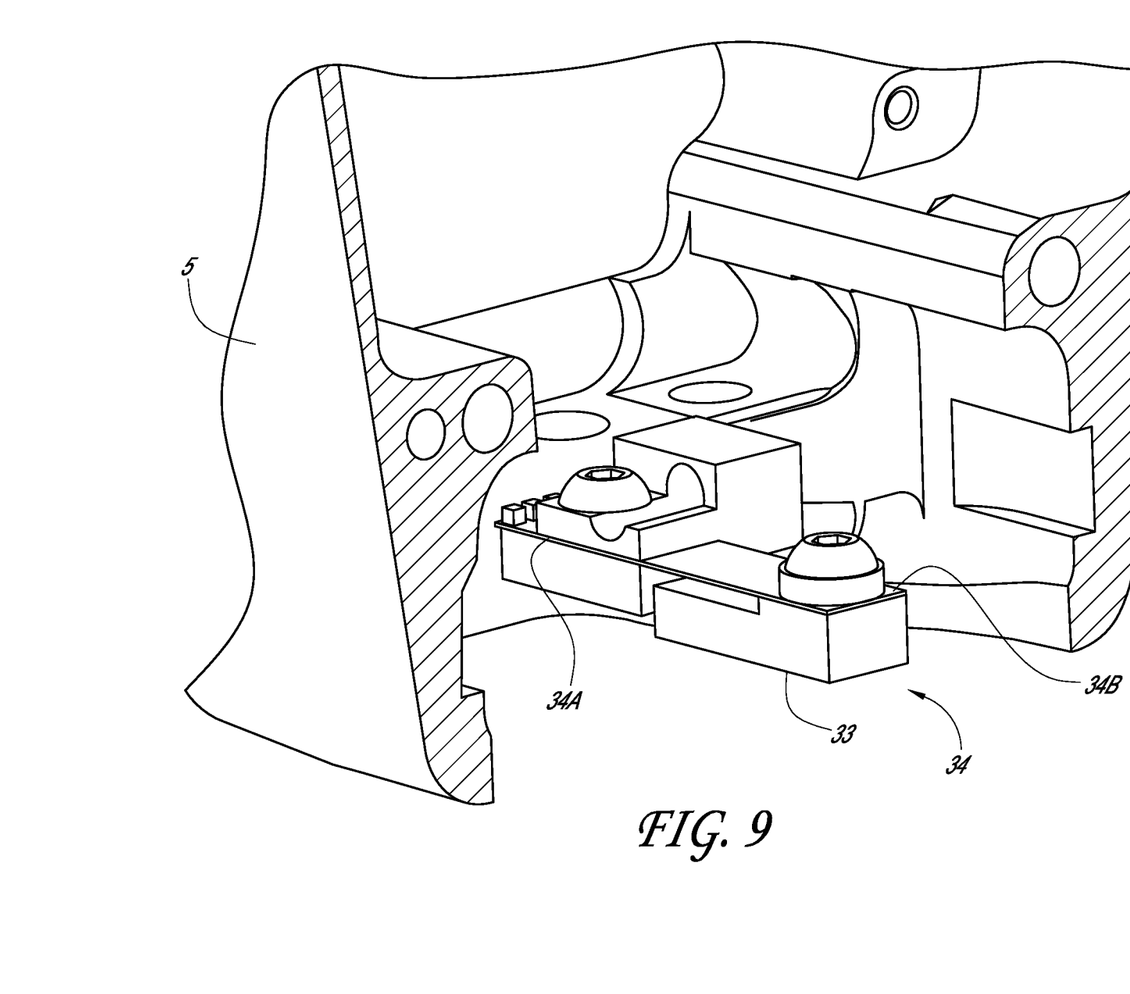
FIG. 9 is a cross-sectional view of the ground contact sensor of the prosthetic knee device of FIG. 1, depicting a load sensor.

The load cell 34 is rigidly mounted to the frame rear part 27 at one end 34A and connected to a displacement transferring block 33 at another end 34B that can be a free end. The displacement transferring block 33) remains in operative contact with the distal dome connector 8 and transfers axial displacement of the distal dome connector 8 to the load cell 34, causing a change of the load cell output that is recorded by a processing system such as a computer controlled system on the prosthetic device 100, another prosthetic or orthotic device, or on a peripheral device. It is to be noted that the use of the displacement transferring block 33 can be directly associated with the use of a thin beam load cell 34 to measure the distal dome connector 8 displacement. In other embodiments, other types of sensors can be used to measure this displacement, with or without a displacement transferring block 33. Other types of sensors that could be used to measure the moving part displacement include, but are not limited to, optical encoders, magnetic switches, magnetic encoders, mechanical switches, capacitive displacement sensors combinations of the same or the like. Nevertheless, in some embodiments a load cell may be particularly advantageous due to its small volume, ease of mounting, and the wide travel range it can measure without requiring very accurate mounting or over-travel protection.

The operation of certain embodiments of the prosthetic devices disclosed herein is now described. Based on the sizes of the parts and the relative positioning of the moving portion 102 of the ground contact sensor with respect to non-moving portions such as the frames 20, 27, the moving portion 102 can be in its fully external position when not submitted to any load. In that position, the front and rear backing plates 32, 36 can rest against the frame sections 20, 27, maintained in this position by a light preload generated by an elastic deformation of the blade sets 14, 18. For example, the front and rear backing plates 32, 36 can have abutment surfaces 54 that can rest against corresponding abutment surfaces on the non-moving portion such as on the tibial shank 5, or more particularly on the front and rear frames 20, 27 of the tibial shank 5.

Loads can then be provided, e.g., by motion of the prosthetic device 100 or external factors. Knee joint motion can be characterized at least partially by two separate zones of high acceleration amplitude sequences. One such zone can occur at a maximum heel rise point, where the knee joint flexion motion first decelerates to control the height at which the foot will lift, followed by an acceleration sequence to initiate the subsequent knee extension. A second acceleration zone can be found at the end of a swing phase, when the knee joint decelerates in order to properly position the limb and foot prior to transitioning to stance phase. As the knee joint is accelerated, or decelerated, to properly sustain the locomotion activity being performed by the user, the prosthetic foot inertia can generate quantifiable anterior-posterior loading on the ground contact sensor moving portion 102. The load in question can take the form of a sagittal plane torque applied on the ground contact sensor moving part, without any axial component, or at least any substantial internally directed axial loading.

When the torque is applied to the ground contact sensor moving portion 102, the effort is distributed between the upper and lower blade groups of the blade sets 14, 18, which can show significant stiffness due to the vertical offset separating these blade groups. The axial displacement of the moving portion 102 of the ground contact sensor resulting from inertial torque application can then be limited to a value significantly lower than what is typically observed when axial loading occurs.

Upon occurrence of a foot strike, weight can be applied on the heel region of the foot, which can cause the blade sets 14, 18 to bend and the moving portion 102 of the ground contact sensor to move within the prosthetic device 100, until part of the moving portion such as a main body of the moving portion (e.g., the distal dome connector 8) hits the frame sections 20, 27. For example, the distal dome connector 8 can include abutment surfaces 62 that can come into contact with corresponding abutment surfaces 64 on the non-moving portion, such as the tibial shank 5, or more particularly the frame sections 20, 27. Once the moving portion 102 of the ground contact sensor has moved to its full extent (e.g., a limited displacement as discussed above), the distal dome connector 8 can be adjacent to and/or in contact with one or both of the front and rear frame sections 20, 27. In turn, the load cell free end 34B can move, causing the sensor output to change, indicating to the system that weight is now applied on the lower-limb prosthetic or orthotic device 100.

As the user's center of mass moves over the prosthetic foot, the line of force on the prosthetic device 100 can move over to the foot-toe region. Migration of the force to the foot-toe region changes the nature of the loading imposed to the moving portion 102 of the ground contact sensor. Instead of the mostly axial load associated with heel loading, loading can now be composed of an axial and a sagittal plane torque component. In that context, the moving portion 102 of the ground contact sensor can shift position in the frame, the rear of the moving portion 102 being pulled out until the rear backing plate 36 (or associated abutment surface 54) comes in contact with the rear frame section 27 (or associated abutment surface 56), hence limiting its travel, while the front of the moving portion 102 remains in the same position as before. The opposite shift can also be observed when the weight line moves toward the heel section of the foot following initial toe strike. However, a short lever associated with the foot-heel section might not allow the torque component to sufficiently rise for this phenomenon to be observed in all embodiments or situations.

As previously discussed, occurrence of frontal plane torque due to the fact that the ground reaction forces are not aligned with a long axis of the prosthetic device 100 can be controlled through the side blocks 13, which can be secured in slots machined in the frame, as best shown in FIG. 6. As the frontal plane torque increases, the moving portion 102 of the ground contact sensor can rotate about its anterior-posterior centerline until both side blocks 13 (or corresponding abutment surfaces 58) contact the frame (or corresponding abutment surfaces 60), hence blocking further rotation of the moving portion 102 in the frontal plane. It is to be noted that, in such embodiments, the side blocks 13 are not limiting the axial travel, only the distal dome connector 8, frame sections 20, 27 and backing plates 32, 36 are used to limit the moving part axial travel in the depicted embodiment. For example, the clearance provided for the limited displacement of the side blocks 13 can be greater than the clearance provided for the limited displacement of the backing plates 32, 36. Thus, in axial movement the backing plates 32, 36 have less room for travel, and thus their corresponding abutment surfaces 54, 56 come into contact under axial loads before the abutment surfaces 58, 60 of the side blocks 13. However, as best shown in FIGS. 3 and 4, the side blocks 13 can be substantially centered along a medial-lateral axis or centerline, whereas the backing plates 32, 36 can be substantially centered about an anterior-posterior axis or centerline. Thus, rotations about these axes will cause differing amounts of total movement for the side blocks 13 and the backing plates 32, 36, based on their displacement from the relevant rotational axis, such that under non-axial loads the side blocks 13 can still partially define the limited displacement.

Figure 10:
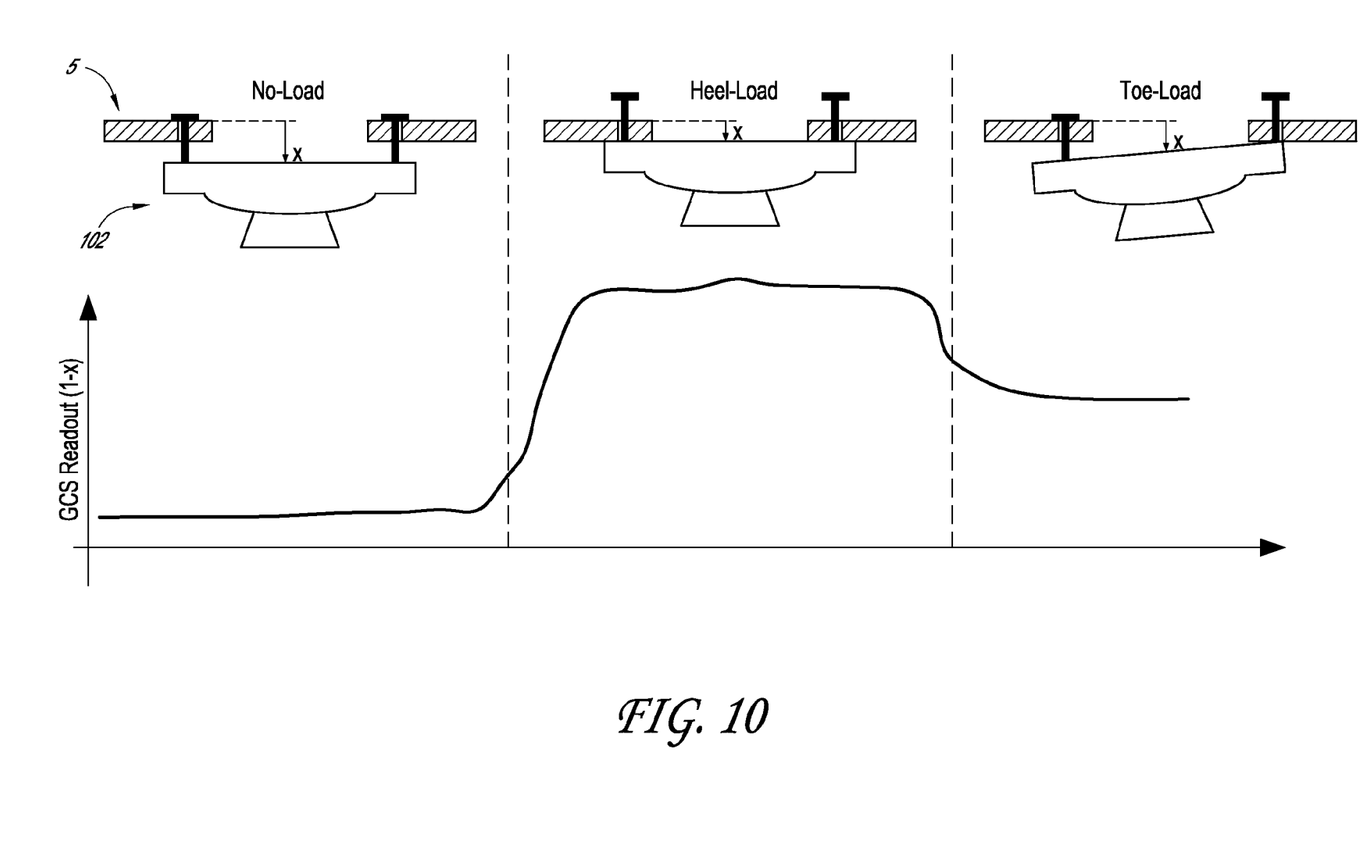
FIG. 10 is representative graph indicating a correspondence between readouts from a load sensor and positions of the ground contact sensor of the prosthetic knee device of FIG. 1.

Due to the relative positioning of the load cell 34 and the displacement transferring block 33 with respect to the moving part's travel stops (e.g., the side blocks 13, backing plates 32, 36, and the frame sections 20, 27), the load cell 34 reading under toe load can be scaled down with respect to what is observed during heel load. FIG. 10 illustrates this last observation, where the typical ground contact sensor output is plotted with respect to the three typical types of moving part positioning based on the load case previously introduced. In FIG. 10, the load sensor 34 can detect load provided at the point denoted by "x". Review of the sensor geometry outlined below illustrates why the load cell signal is scaled down under toe load condition. For example, it is noted that the load sensor 34 is positioned substantially at the center or rotational axis in the anterior-posterior direction, as depicted in FIG. 6. Thus, it is substantially unaffected by rotations about this axis (such as that shown under toe-load). However, the toe-load can also cause a translation on one side of the device (in addition to this rotation). Thus, the displacement felt at the load sensor can be approximately half that measured under heel-load.

Although the ground contact sensor methods and systems disclosed herein have been described with reference to particular embodiments, it will be understood that such inventive systems and methods can be used with a wide variety of prosthetic and/or orthotic systems. For example, the embodiments of a ground contact sensor disclosed herein can be used in connection with various types of motion-controlled or passive knee and/or ankle prosthetic or orthotic devices, such as the motion-controlled prosthetic feet described in U.S. Pat. No. 7,637,959, issued Dec. 29, 2009, or the motion-controlled knee described in U.S. Patent Application Publication No. 2009/0299480, published Dec. 3, 2009, which are both hereby incorporated herein by reference in their entirety to be considered part of this specification. In some embodiments, the ground contact sensor can be a modular device, such that the non-moving portion is, e.g., separable from a tibial shank and can then be applied to other devices. In some embodiments such a modular ground contact sensor can be threadably attached to a prosthetic knee, foot, or other device.

Moreover, information gathered from the ground contact sensor can be utilized, alone or in combination with other sensor measurements (e.g., load sensors, pressure sensors, accelerometers, gyroscopes, GPS sensors, motion sensors, etc.) in the real-time analysis of a user's gait, automatic control of a prosthetic knee and/or ankle, evaluation of the alignment and/or performance of the prosthetic or orthotic device, and/or to predict or anticipate a terrain change that requires a change in the user's locomotion. Further, in some embodiments the sensors disclosed herein can be used for purposes other than sensing contact with the ground, such as sensing contact against a wall, with a projectile, or some other force.

The blocks or states of the processes or methods described herein may be embodied directly in hardware, in a software module executed by a processor, or in a combination of the two. In certain embodiments, the processor may be located at least partially on, in or remote to the prosthetic or orthotic device comprising the ground contact sensor. Moreover, readings from the ground contact sensor can be downloaded or wirelessly transmitted to a remote computing device for further analysis of the user's gait. In other embodiments, multiple ground contact sensors can be used with a prosthetic or orthotic device, e.g., to at least partially control the device.

For example, processes described herein may also be embodied in, and fully automated by, software modules executed by one or more machines such as computers or computer processors. A module may reside in any form of computer-readable (e.g., storage) medium known in the art. An exemplary computer-readable medium can be coupled to a processor such that the processor can read information from, and write information to, the computer-readable medium. In the alternative, the computer-readable medium may be integral to the processor.

Depending on the embodiment, certain acts, events, or functions of any of the processes or algorithms described herein can be performed in a different sequence, may be added, merged, or left out all together. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it may be understood that various omissions, substitutions, and changes in the form and details of the ground contact sensing system, including the sensor components, logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others.

What is claimed is:

1. A ground-contact sensor comprising:
    a non-moving body comprising:
        two or more non-moving abutment surfaces disposed on separate sides of the non-moving body; and
        a load cell mounted to the non-moving body at a first end and comprising a second end;
    a moving body configured to receive a load, the moving body comprising:
        two or more moving abutment surfaces disposed generally adjacent to the non-moving abutment surfaces to allow a limited displacement between the abutment surfaces, at the abutment surfaces; and
        a load cell receiving portion disposed generally between the abutment surfaces and operatively mounted to the second end of the load cell such that the load cell can sense a relative displacement between the non-moving and moving bodies,
    wherein an axial load applied to the moving body can cause the moving body to move relative to the non-moving body and the moving abutment surfaces to move relative to the non-moving abutment surfaces said limited displacement, which can cause a first displacement sensed by the load cell, and
    wherein a torsional load applied to the moving body can cause the moving body to rotate relative to the non-moving body and at least one moving abutment surface to move relative to the corresponding non-moving abutment surface said limited displacement, which can cause a second displacement sensed by the load cell different from the first displacement.

2. The ground-contact sensor of claim 1, wherein the first displacement is greater than the second displacement.

3. The ground-contact sensor of claim 2, wherein the second displacement is approximately half of the first displacement.

4. The ground-contact sensor of claim 1, wherein the limited displacement is less than 1 mm.

5. The ground-contact sensor of claim 1, further comprising one or more elongated bodies extending in a direction substantially parallel to a line between the abutment surfaces, the one or more elongated bodies being rigidly mounted at opposite side portions to the non-moving body and rigidly mounted at a middle portion to the moving body.

6. The ground-contact sensor of claim 5, wherein the one or more elongated bodies are configured to resiliently bend when a load is applied to the moving body.

7. The ground-contact sensor of claim 1, wherein the non-moving body further comprises two secondary non-moving abutment surfaces oriented generally perpendicular to the abutment surfaces and on separate sides of the non-moving body, and the moving body comprises two secondary moving abutment surfaces corresponding to said secondary non-moving abutment surfaces to allow a limited displacement between the secondary abutment surfaces.

8. The ground-contact sensor of claim 7, wherein the secondary abutment surfaces allow for a limited displacement greater than the limited displacement between the abutment surfaces.

9. A prosthetic lower limb device comprising the ground-contact sensor of claim 1.

10. The prosthetic lower limb device of claim 9, wherein the prosthetic lower limb device is actively actuated, at least partially in response to loads sensed by the load cell.

11. The prosthetic lower limb device of claim 9, wherein the prosthetic lower limb device comprise a prosthetic knee.

12. The prosthetic lower limb device of claim 9, wherein the axial load corresponds to heel-ground contact and the torsional load corresponds to toe-ground contact.

13. A ground contact sensor for a prosthetic or orthotic device, comprising:
    a connector movably attachable to a frame portion of the prosthetic or orthotic device, the connector axially and pivotally movable relative to the frame portion, the connector further comprising:
        a first pair of planar blades disposed on a medial side of the distal connector and extending in an anterior-posterior direction, the first pair of planar blades being axially spaced apart from each other, and
        a second pair of planar blades disposed on a lateral side of the distal connector and extending in the anterior-posterior direction, the second pair of planar blades being axially spaced apart from each other,
        the first and second pair of blades configured to resiliently flex when the prosthetic or orthotic device is subjected to a load; and
    a load sensor receiving portion configured to couple to a load sensor on the prosthetic or orthotic device, the load sensor configured to sense relative movement between the connector and the frame portion during operation of the prosthetic or orthotic device,
    wherein the connector is configured to axially displace relative to the frame portion when the frame portion is subjected to an axial load such that at least a portion of the first and second pair of blades flex, the load sensor sensing said axial displacement between the connector and the frame portion, and wherein the connector rotates about a second axis, perpendicular to the longitudinal axis, relative to the frame portion when the frame portion is subjected to a torsional load such that at least a portion of the first and second pair of blades flex, the load sensor sensing said rotation.

14. The ground contact sensor of claim 13, wherein a connector comprises two or more abutment surfaces configured to about two or more abutment surfaces on the frame portion configured to limit the axial displacement of the connector relative to the frame portion.

15. The ground contact sensor of claim 13, further comprising a block between each pair of blades to define the axial spacing between said blades.

16. The ground contact sensor of claim 13, wherein the blades are configured to rigidly mount to the frame at end portions of the blades.

17. A prosthetic lower limb device comprising the ground-contact sensor of claim 13.

18. The prosthetic lower limb device of claim 17, wherein the prosthetic lower limb device is actively actuated, at least partially in response to loads sensed by the load cell.

19. The prosthetic lower limb device of claim 17, wherein the prosthetic lower limb device comprise a prosthetic knee.

20. The prosthetic lower limb device of claim 17, wherein the axial load corresponds to heel-ground contact and the torsional load corresponds to toe-ground contact.

\* \* \* \* \*